US012700486B1

(12) United States Patent
Arkoff et al.

(10) Patent No.:  US 12,700,486 B1
(45) Date of Patent:      Aug. 4, 2026

(54) SYSTEM FOR GOVERNANCE OF MEDICAL DATA WITH SECURE CAPTURE, VALIDATION, NORMALIZATION, EXPORT, AND COMPLIANCE AUDITING INCLUDING AI INTEGRATION ACROSS MEDICAL SYSTEMS

(71) Applicant: OneSource Solutions International, Inc., Sudbury, MA (US)

(72) Inventors: Harold Arkoff, Sudbury, MA (US); Vedran Jukic, Trieste (IT)

(73) Assignee: OneSource Solutions International, Inc., Sudbury, MA (US)

( * ) Notice: Subject to any disclaimer, the term of this patent is extended or adjusted under 35 U.S.C. 154(b) by 0 days.

(21) Appl. No.: 19/354,703

(22) Filed: Oct. 9, 2025

Related U.S. Application Data

(63) Continuation-in-part of application No. 19/221,392, filed on May 28, 2025, now Pat. No. 12,464,027.

(51) Int. Cl.
G16H 10/65          (2018.01)
H04L 9/32            (2006.01)

(52) U.S. Cl.
CPC ........... G16H 10/65 (2018.01); H04L 9/3213 (2013.01); H04L 9/3247 (2013.01)

(58) Field of Classification Search
CPC ...... G16H 10/65; H04L 9/3213; H04L 9/3247
USPC .......................................................... 705/3
See application file for complete search history.

(56) References Cited

U.S. PATENT DOCUMENTS

| | | | | |
|---|---|---|---|---|
| 6,804,787 | B2 * | 10/2004 | Dick .................. | H04N 1/00204 |
| | | | | 726/28 |
| 7,668,820 | B2 * | 2/2010 | Zuleba ................ | G06F 21/6227 |
| | | | | 707/765 |
| 9,886,558 | B2 * | 2/2018 | Ober ..................... | G06F 16/248 |
| 11,080,423 | B1 * | 8/2021 | Kassam-Adams ..... | G16H 15/00 |
| 11,532,393 | B2 * | 12/2022 | Arkoff .................. | G16H 40/67 |
| 11,693,990 | B1 * | 7/2023 | Arkoff .................. | G06F 21/602 |
| | | | | 726/26 |

(Continued)

*Primary Examiner* — Michael Tomaszewski
(74) *Attorney, Agent, or Firm* — IP Consulting Group; Michael Razavi; Alfred F. Hoyte

(57)                    ABSTRACT
A system for medical data governance that unifies secure capture, validation, arbitration, and export of multimodal patient data in regulated environments. The system comprises secure capture modules configured to ingest high-frequency clinical inputs, validation subsystems that apply patient identification and schema enforcement, and a central repository that normalizes governed datasets. Data are bound to compliance tokens carrying provenance, jurisdictional metadata, and cryptographic signatures. Outputs are processed by arbitration engines that resolve conflicting AI analyses under encoded policy thresholds. Glyph rendering subsystems generate visual, auditory, haptic, or machine-readable indicators of consent, compliance, or override events, each tied to immutable audit records. An append-only ledger records token issuance, arbitration decisions, and export transactions, including ANSI X12 billing flows, with cascading revocation across federated validators. The disclosed architecture ensures that governed inputs and outputs remain verifiable, auditable, and enforceable, enabling trustworthy AI deployment in clinical and regulatory settings.

12 Claims, 4 Drawing Sheets

(56) References Cited

U.S. PATENT DOCUMENTS

| | | | | |
|---|---|---|---|---|
| 11,699,044 B1* | 7/2023 | Allen | G06V 30/19147 | 704/9 |
| 11,755,760 B2* | 9/2023 | Balan | H04L 63/101 | 726/1 |
| 2002/0026332 A1* | 2/2002 | Snowden | G06Q 10/10 | 705/3 |
| 2002/0111833 A1* | 8/2002 | Dick | G16H 10/60 | 705/3 |
| 2002/0116227 A1* | 8/2002 | Dick | G16H 10/60 | 705/3 |
| 2004/0117215 A1* | 6/2004 | Marchosky | G16H 10/60 | 705/3 |
| 2005/0182655 A1* | 8/2005 | Merzlak | G16H 50/70 | 705/2 |
| 2005/0192843 A1* | 9/2005 | Pratt | G06Q 10/10 | 705/3 |
| 2005/0192844 A1* | 9/2005 | Esler | G16H 70/00 | 705/3 |
| 2007/0061487 A1* | 3/2007 | Moore | G06F 16/27 | 707/E17.032 |
| 2008/0046292 A1* | 2/2008 | Myers | G06F 16/283 | 705/3 |
| 2008/0183495 A1* | 7/2008 | Butterfield | G16H 10/60 | 715/742 |
| 2008/0208625 A1* | 8/2008 | Joseph | G16H 40/67 | 705/2 |
| 2008/0215627 A1* | 9/2008 | Higgins | G16H 10/60 | |
| 2013/0124222 A1* | 5/2013 | Nashtut | G06Q 10/10 | 705/3 |
| 2014/0188515 A1* | 7/2014 | Mansker | G16H 30/20 | 705/3 |
| 2014/0257047 A1* | 9/2014 | Sillay | H04L 63/10 | 600/595 |
| 2015/0058627 A1* | 2/2015 | Paffel | G16H 10/60 | 713/168 |
| 2015/0149362 A1* | 5/2015 | Baum | G06F 21/602 | 705/51 |
| 2015/0161413 A1* | 6/2015 | Calem | G06F 21/6245 | 705/51 |
| 2016/0019348 A1* | 1/2016 | Boston | G16Z 99/00 | 705/3 |
| 2016/0378919 A1* | 12/2016 | McNutt | G16H 40/63 | 705/3 |
| 2017/0249432 A1* | 8/2017 | Grantcharov | G06F 1/12 | |
| 2017/0374067 A1* | 12/2017 | Quintas | H04L 63/20 | |
| 2018/0122506 A1* | 5/2018 | Grantcharov | H04L 63/0421 | |
| 2018/0232526 A1* | 8/2018 | Reid | G06F 21/6218 | |
| 2019/0294822 A1* | 9/2019 | Hennebert | G06F 21/602 | |
| 2019/0385743 A1* | 12/2019 | Rasmussen | G16B 40/20 | |
| 2020/0160946 A1* | 5/2020 | Poblenz | G06Q 10/06315 | |
| 2020/0251225 A1* | 8/2020 | Murrish | G06F 16/951 | |
| 2020/0356694 A1* | 11/2020 | Lee | H04L 9/3263 | |
| 2020/0401727 A1* | 12/2020 | Hennessy | H04L 9/50 | |
| 2021/0050104 A1* | 2/2021 | Arkoff | G16H 40/67 | |
| 2021/0076966 A1* | 3/2021 | Grantcharov | G06N 20/00 | |
| 2022/0329436 A1* | 10/2022 | Gaur | H04L 9/50 | |
| 2023/0197214 A1* | 6/2023 | Arkoff | G16H 10/60 | 705/3 |
| 2023/0328104 A1* | 10/2023 | Ghosh | H04W 4/021 | 726/23 |
| 2026/0121859 A1* | 4/2026 | Arkoff | G06F 21/6245 | |

* cited by examiner

GOVERNANCE-BASED SYSTEM (100)

HIGH-FREQUENCY PATIENT DATA SYSTEM (200)

AI EXPORT AND INTEGRATION SYSTEM (300)

COMPLIANCE AUDITING AND IMMUTABLE REGISTRY (400)

SYSTEM FOR GOVERNANCE OF MEDICAL DATA WITH SECURE CAPTURE, VALIDATION, NORMALIZATION, EXPORT, AND COMPLIANCE AUDITING INCLUDING AI INTEGRATION ACROSS MEDICAL SYSTEMS

CROSS-REFERENCE TO RELATED APPLICATIONS

This application is a continuation-in-part (CIP) of U.S. patent application Ser. No. 19/221,392, filed May 28, 2025, entitled "System and Method for Policy-Constrained Symbolic Rendering of AI Outputs." application Ser. No. 19/221,392 is itself a continuation-in-part of U.S. patent application Ser. No. 17/993,765, filed Nov. 23, 2022, now issued as U.S. Pat. No. 12,327,634, entitled "Operating Room Management System with Mobile Application."

This application is also related to U.S. Pat. No. 11,693,990, issued Jul. 4, 2023, from U.S. patent application Ser. No. 16/812,282, filed Mar. 7, 2020, entitled "Medical Data Governance."

This application is further related to U.S. patent application Ser. No. 19/278,692, filed Jul. 23, 2025, entitled "System for Federated Compliance-Token Inheritance, Digital Artifact Registry, and Monetization in Regulated Environments Using Large Language Models."

FIELD OF THE INVENTION

The present invention relates to systems for governance of medical data in regulated clinical environments. More particularly, it concerns a system-level architecture comprising secure capture, validation, normalization, storage, and export of multimodal patient data; generation of cryptographically bound compliance records and audit logs; and integration of governed datasets with artificial intelligence subsystems and heterogeneous medical platforms.

BACKGROUND OF THE INVENTION

The collection and integration of medical device data has been a longstanding challenge in clinical environments. Hospitals and healthcare systems typically operate thousands of heterogeneous devices and subsystems, each generating data in proprietary formats with inconsistent identifiers, timestamps, and metadata. Attempts to consolidate such data into a coherent and auditable patient record have historically failed to achieve completeness, accuracy, and regulatory compliance.

By 2019, despite decades of investment by major vendors, the problem remained unresolved. General Electric had attempted for years to build interoperable medical device data integration platforms, but ultimately abandoned the effort without delivering a sustainable solution. Philips, despite being a global leader in medical devices, lacked an internally developed system and was compelled to spend approximately $635 million to acquire Capsule Corporation in 2021. Even after this acquisition, Philips and its competitors continued to struggle with data validation, normalization, and governance across distributed hospital systems.

The emergence of the COVID-19 pandemic in 2020 dramatically amplified these challenges. Hospitals were suddenly required to deploy vast numbers of additional devices across intensive care units, emergency departments, and temporary facilities, leading to even greater fragmentation of data sources. Rather than converging toward a homogeneous platform, hospitals found themselves with an even more diverse and incompatible array of systems. The lack of interoperability and governance became acute, undermining the ability of providers to build accurate patient records or demonstrate regulatory compliance.

At the same time, artificial intelligence systems began to emerge as critical clinical and operational tools. However, without medical data governance, these AI systems could not be trusted: their inputs were inconsistent, unverifiable, and non-compliant. In this context, AI adoption in healthcare was effectively blocked. The absence of a governance framework meant that no AI system could safely or legally operate across hospital data streams.

Accordingly, there exists a clear and unmet need for a system that enforces governance at every stage of the medical data lifecycle. Such a system must provide secure data capture, validation, normalization, export, and cryptographic auditing, while enabling interoperability across heterogeneous medical subsystems and ensuring compliance with regulatory mandates. The present invention, described in detail in Section 6, directly addresses these deficiencies by introducing a system-level governance architecture that solves the interoperability, compliance, and trustworthiness problems that prior art systems failed to overcome.

SUMMARY OF THE INVENTION

The present invention addresses these deficiencies by introducing a governance-based system for secure capture, validation, storage, normalization, export, and cryptographic auditing of medical device data. The invention integrates secure capture modules (including digital black boxes, device interfaces, and manual approval interfaces), a patient identification and data validation subsystem, a central repository, a data analysis engine, and export driver modules to ensure that complete and accurate patient data can be delivered across heterogeneous subsystems.

Unlike prior attempts, the invention enforces governance at every stage of the data lifecycle. Each data object inherits governance metadata including provenance identifiers, jurisdictional codes, and cryptographic attributes. Data exports are bound to compliance tokens and logged in an immutable audit ledger, ensuring non-repudiation and regulatory verifiability.

This system enables healthcare providers to securely integrate high-frequency data streams, feed normalized records into artificial intelligence subsystems, and demonstrate compliance with regulatory frameworks such as HIPAA, CMS, FDA, GDPR, and the EU AI Act. The invention therefore establishes the technological backbone for trustworthy AI in healthcare.

In particular, the invention provides the critical keystone infrastructure necessary for hospitals to adopt AI. Without medical data governance, AI adoption is unsafe, unreliable, and non-compliant. With the invention disclosed herein, hospitals can finally trust their data streams, regulators can audit compliance, and AI systems can operate on accurate and verifiable patient data. This technological leap provides the necessary foundation for the safe deployment of AI in healthcare.

BRIEF DESCRIPTION OF THE DRAWINGS

The accompanying drawings, which are incorporated in and constitute a part of this specification, illustrate embodiments of the invention and, together with the written description, serve to explain the principles of the invention. In the drawings.

DETAILED DESCRIPTION OF THE INVENTION

The following detailed description is provided to enable any person skilled in the art to make and use the invention and sets forth the best mode contemplated by the inventor for carrying out the invention. The invention may be embodied in many different forms and should not be construed as limited to the examples set forth herein.

Figure 1:
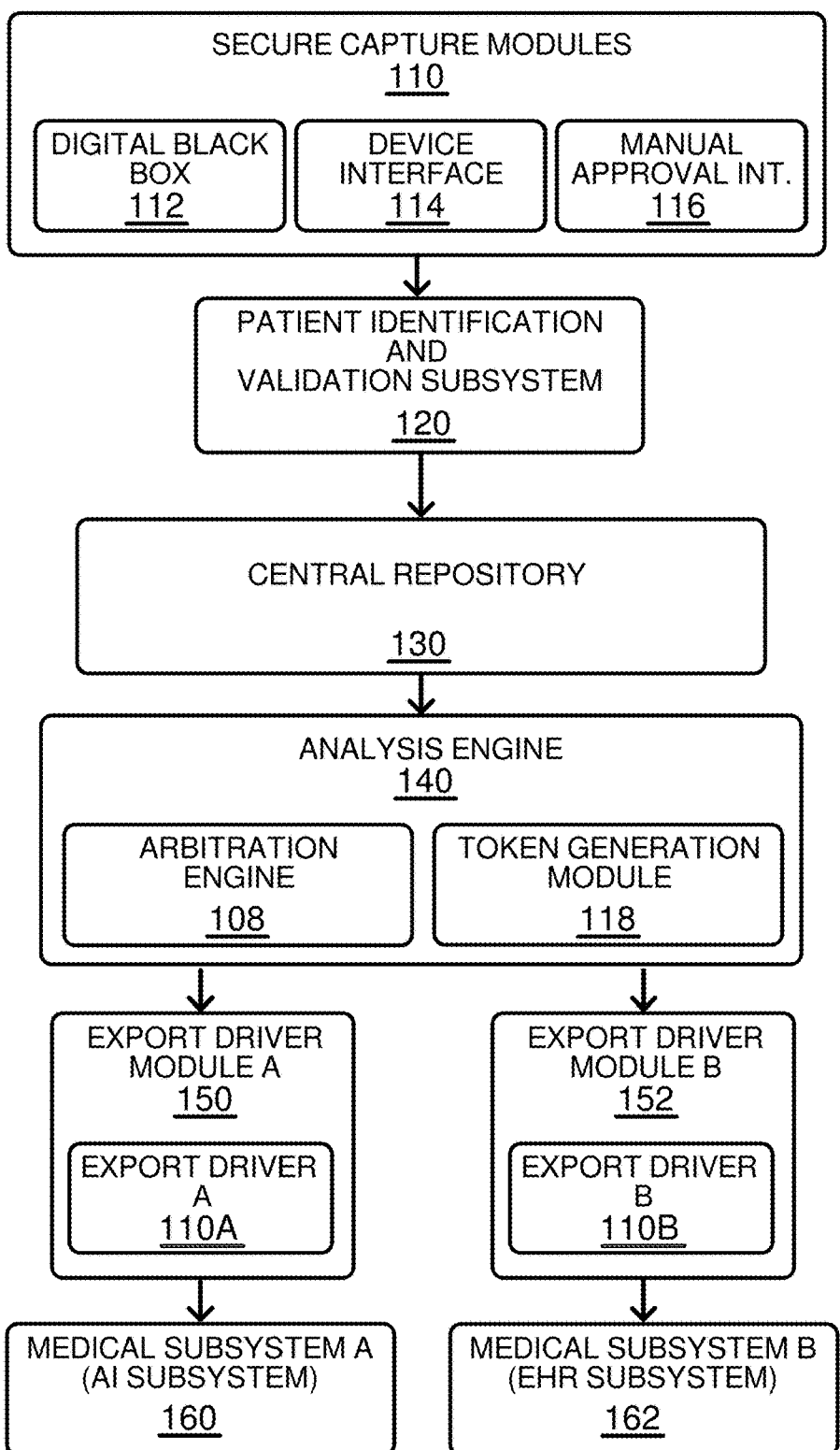
FIG. 1 is a block diagram illustrating a governance-based system architecture including secure capture modules configured to ingest multimodal patient data, a patient identification and validation subsystem, a central repository, a data analysis engine, and export driver modules configured to provide data to heterogeneous downstream subsystems.
Figure 2:
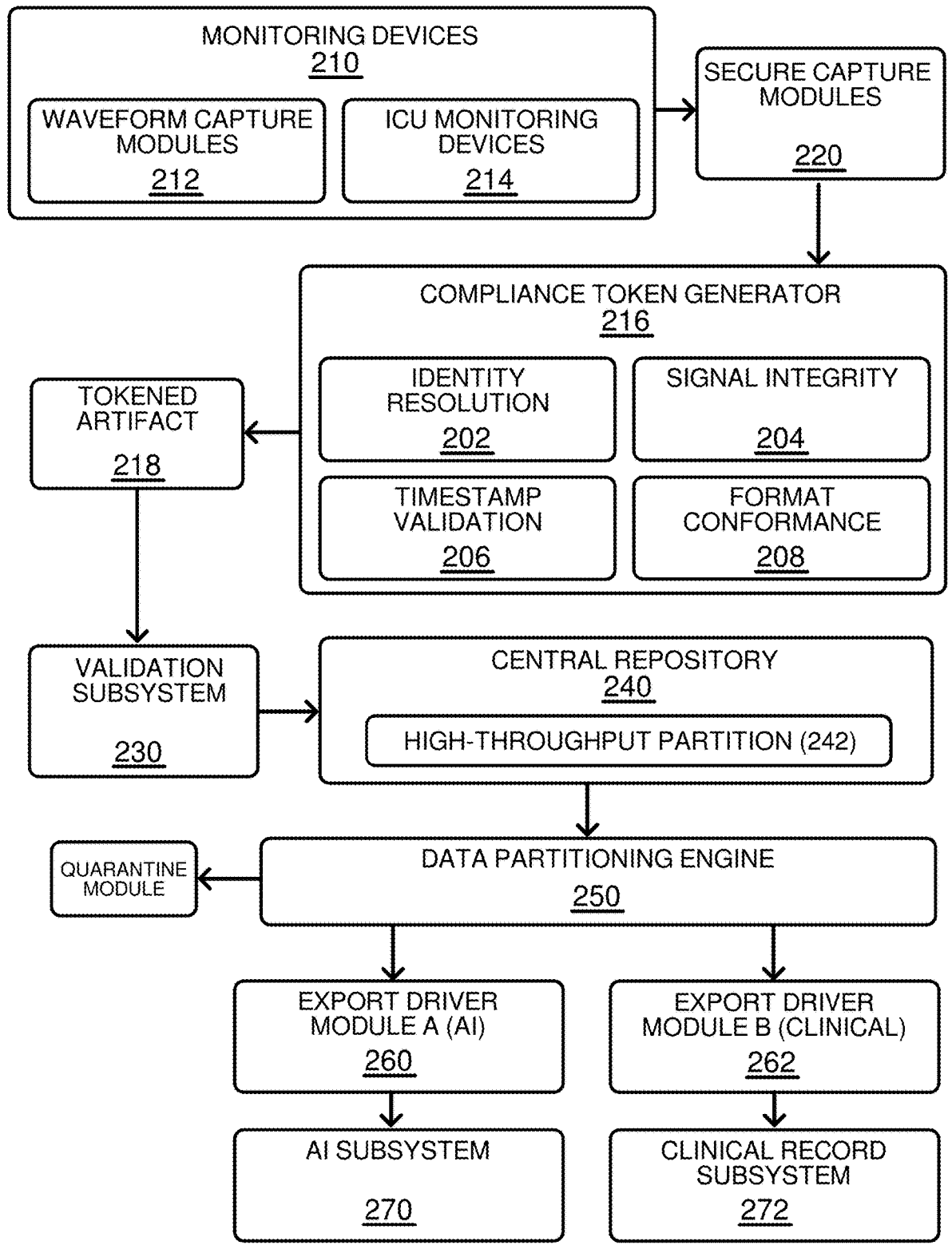
FIG. 2 is a block diagram illustrating a system for handling high-frequency patient data streams, including waveform and ICU monitoring devices coupled to secure capture modules, a validation subsystem, a central repository with partitioning for streaming data, and export driver modules configured to route high-frequency subsets to artificial intelligence and clinical record subsystems.
Figure 3:
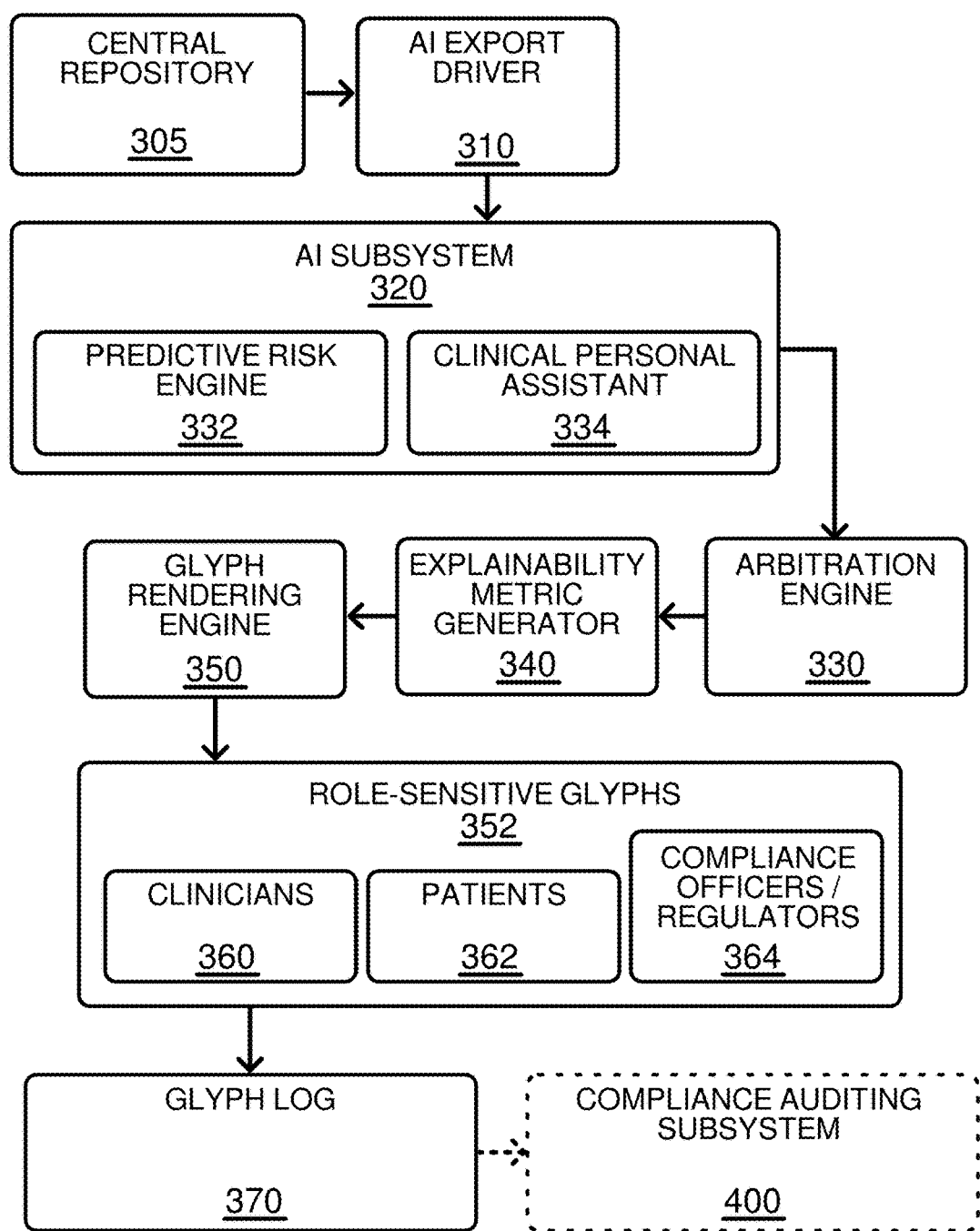
FIG. 3 is a block diagram illustrating a system for exporting normalized data from the central repository to an artificial intelligence subsystem, including a personal assistant module, an explainability metric generator, a glyph rendering engine configured to produce role-sensitive glyphs, and an audit log for recording outputs and glyph events.

Although FIGS. 1-4 are described separately for clarity, the applicant regards them as interoperable embodiments of a single inventive concept. Each embodiment relies on the same compliance token schema, arbitration logic, governance metadata, and immutable audit logging. For example, the secure capture and validation functions disclosed in FIG. 1 supply governed streams into the high-frequency partitioning and tokenization workflows of FIG. 2; the outputs of FIG. 2 feed into the AI export and glyph rendering subsystems of FIG. 3; and the glyph events and governed outputs of FIG. 3 are recorded and audited within the compliance infrastructure of FIG. 4. Thus, while disclosed modularly, these embodiments are interdependent subsystems of one unified governance architecture for medical data.

Overview

The invention provides a system-level architecture for real-time governance, validation, arbitration, and transformation of medical data and AI outputs in regulated environments. The system establishes trust in patient-linked data streams by ensuring that captured inputs are: (i) securely ingested with provenance guarantees, (ii) positively identified and validated against patient identity, (iii) normalized and analyzed to remove protected health information (PHI) and correct association errors, (iv) governed via cryptographically bound compliance tokens, (v) arbitrated when multiple governed outputs conflict, and (vi) exported to heterogeneous subsystems using format-specific export drivers while preserving compliance lineage and auditability.

As used herein, a digital black box (also termed a secure capture module) is a hardware and/or software subsystem for fault-tolerant acquisition of multimodal clinical inputs (e.g., physiologic waveforms, device telemetry, environmental metadata, audio, and/or video) under synchronized timestamps with tamper-resistant logging and encryption at the point of capture. Modules may include redundant logging buffers, integrity hash-chaining, and monotonic clock sources to maintain continuity across reboots and network partitions.

Each ingested data object is automatically tagged with governance metadata (provenance identifiers, cryptographic attributes, jurisdictional codes) that persist throughout the object's lifecycle so that downstream processing inherits, verifies, and enforces policy lineage. A version-controlled policy repository expressed in machine-readable grammar is queried by an orchestration engine in real time; if any proposed operation violates current policy, execution is halted or rerouted under provisional constraints (fail-safe).

Federated validators are deployed at subsystem boundaries (e.g., EHR, bedside monitors, imaging, external analytics). These validators enforce schema conformance and governance grammar, apply anomaly detection where applicable, and route non-conforming artifacts to a quarantine module (segregated partition/queue/container) with immutable logging of rejection reason codes.

Validated artifacts are bound to compliance tokens whose fields may include identifiers, jurisdictional tags, timestamps, hashes, policy constraints, escalation codes, schema/version identifiers, and digital signatures (e.g., HSM/TEE anchored). Tokens support issuance, renewal, expiration, and revocation, with cascading invalidation enforced by federated validators and recorded in an immutable audit ledger (e.g., Merkle-linked log). Where multiple AI systems produce governed outputs for the same context, an arbitration engine resolves conflicts using deterministic precedence, threshold gating (e.g., explainability/confidence), and policy-governed stochastic weighting encoded in token fields. Outcomes are cryptographically signed and logged.

The system supports symbolic glyph rendering (visual, auditory, haptic, machine-readable) tied cryptographically to governance events (e.g., consent state, regulatory predicates, break-glass overrides). Role-sensitive glyphs adapt presentation per viewer role while remaining bound to a unified audit record. A glyph log records glyph identifier, timestamp, role context, event type, signature, and ledger reference; glyph libraries may be version-controlled and signed. In fail-safe mode, execution is denied or degraded if required validations, tokens, or glyph acknowledgments cannot be verified.

As used herein, the central repository (e.g., [130], [240], [305]) is a governed data store for validated and normalized patient data, which supports controlled read/write operations, schema enforcement, and retention management. By contrast, the immutable audit ledger (e.g., [430]) is a distinct subsystem dedicated to compliance logging. The immutable audit ledger records governance events, compliance token issuance, arbitration outcomes, export transactions, and revocation cascades in an append-only, cryptographically linked structure. The central repository and the immutable audit ledger are therefore separate and non-overlapping components: the repository provides clinical data access, while the audit ledger provides regulatory verifiability.

FIG. 1—System Architecture

FIG. 1 is a block diagram of a governance-based system (100). The system includes one or more secure capture modules (110), each of which may comprise a digital black box (112), a device interface (114), or a manual approval interface (116). The secure capture modules (110) are connected to a patient identification and validation subsystem (120) configured to associate patient identifiers with incoming data and perform integrity checking. The validated data are stored in a central repository (130). A data analysis engine (140) is coupled to the central repository (130) and configured to remove personal health information, analyze data affinity, and correct association errors. One or more export driver modules (150, 152) are connected to the analysis engine (140) and central repository (130). Each export driver module formats data according to a distinct receiving medical subsystem (160, 162) having a different receipt format. Arrows between modules indicate bidirectional or unidirectional data flows, with provenance and governance metadata attached at each stage.

FIG. 1 depicts end-to-end governance. Secure capture modules (110) ingest multimodal inputs under synchronized timestamps and tamper-resistant logging. Patient identification and data validation occurs in a validation processor (120) performing identity resolution (biometric and deterministic), signal integrity checks, timestamp coherence, and schema conformance. Validated artifacts are stored in a central repository (130) with authenticated access, key management (e.g., HSM), and retention controls aligned to jurisdictional mandates. A data analysis engine (140) de-identifies PHI where required, detects data affinity/association errors, and computes confidence/quality metrics for downstream gating.

An arbitration engine (108) evaluates governance metadata and policy constraints to determine routing to export drivers. A token generation module (118) binds governed artifacts to compliance tokens with signatures produced in an HSM/TEE. Export driver A (110A) normalizes governed outputs for a first receiving medical subsystem (for example an AI subsystem) (160); export driver B (110B) formats outputs for a second receiving medical subsystem (for example an EHR subsystem) (162). Each driver implements delivery assurance, acknowledgments, and schema checks; failures trigger fail-safe routing to quarantine with immutable event logging. The orchestration engine consults the policy repository to enforce real-time constraints across all components.

The validated outputs of the system architecture of FIG. 1 are consumed by the high-frequency processing subsystem of FIG. 2 and the AI export and glyph rendering subsystem of FIG. 3, both of which rely on the compliance tokens and governance metadata first established here.

FIG. 2—High-Frequency Data Flow

FIG. 2 shows ingestion and governance of high-frequency streams (e.g., waveforms, ICU monitors). Devices feed secure capture modules that apply synchronized timestamps, loss-aware buffering, and integrity hash-chaining. High-frequency data passes through identity resolution (202), signal integrity (204), timestamp validation (206), and format conformance (208). The compliance token generator (216) attaches jurisdictional tags, policy constraints, schema version identifiers, and cryptographic signatures, producing a signed tokened artifact (218). Sub-streams may be partitioned for AI analysis and clinical records. Non-conforming samples/events are diverted to quarantine with cause codes (schema mismatch, continuity failure, or integrity violation) and ledger entries sufficient for forensic reconstruction.

Figure 4:
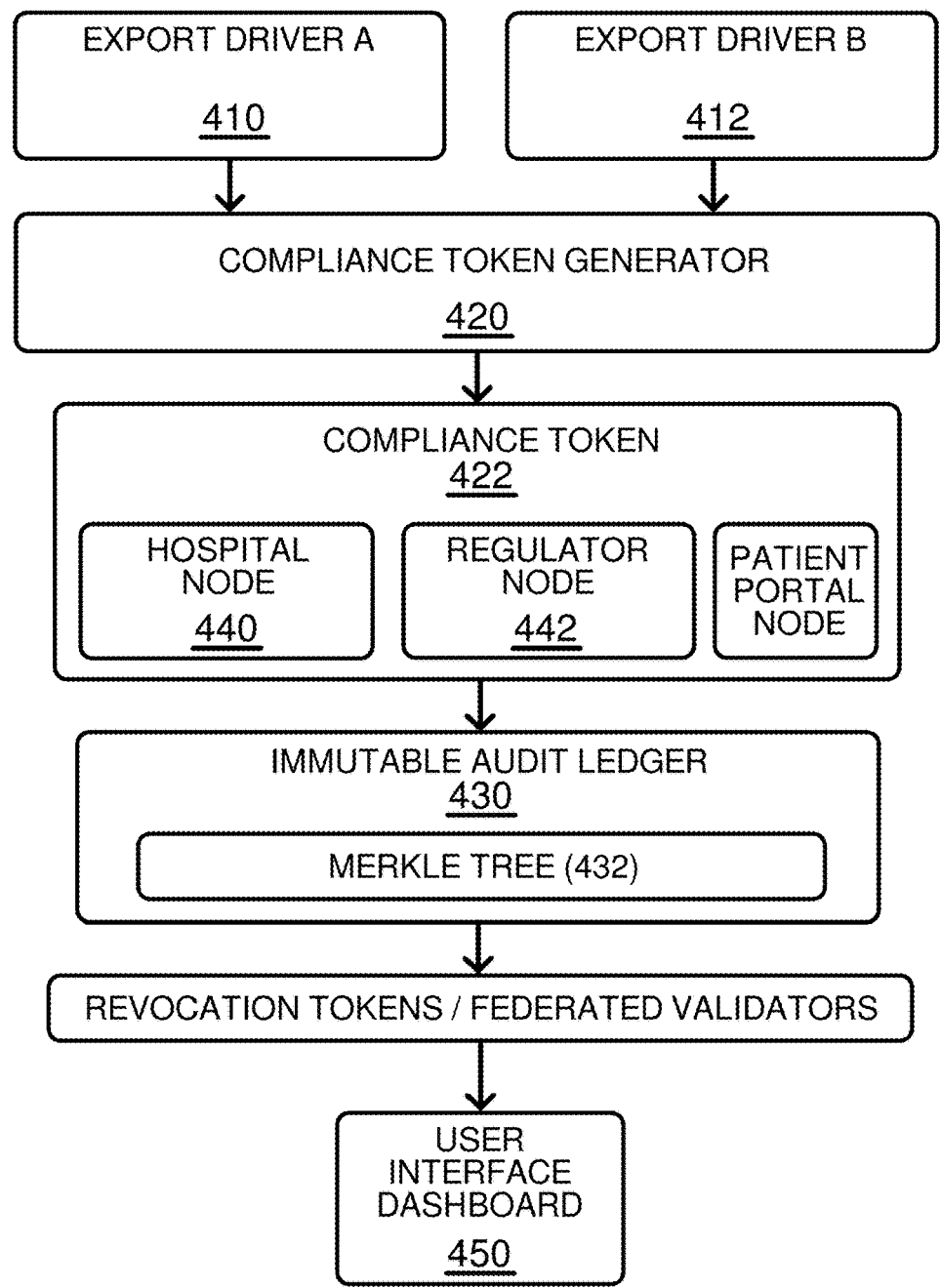
FIG. 4 is a block diagram illustrating a compliance auditing system, including export driver modules, a compliance token generator, and an immutable audit ledger implemented as a Merkle tree, with compliance tokens cross-signed by a hospital node and a regulator node to ensure non-repudiation and regulator verifiability.

The governed high-frequency streams described in FIG. 2 are exported into the AI subsystem of FIG. 3 for explainability analysis and glyph rendering, and all resulting glyph events and arbitration outcomes are immutably logged in the compliance auditing infrastructure of FIG. 4.

FIG. 3—AI Export and Assistant Integration

FIG. 3 is a block diagram of an AI export and integration system (300). A central repository (305) containing validated and normalized data is connected to an export driver (310). The export driver (310) transmits data to an artificial intelligence subsystem (320). The AI subsystem (320) may comprise a predictive risk engine (332) or a clinical personal assistant (334). An explainability metric generator (340) is coupled to the AI subsystem (320) and configured to produce confidence scores or interpretability indicators. These explainability metrics are processed by a glyph rendering engine (350), which outputs role-sensitive glyphs (352) for different users such as clinicians (360), patients (362), or compliance officers (364). All outputs and glyph events are recorded in a glyph log (370), which includes timestamps and cryptographic signatures.

FIG. 3 illustrates integration with an AI personal assistant. Normalized governed datasets are exported via driver A to an AI subsystem. The AI subsystem emits outputs accompanied by explainability metrics or safety/confidence indicators, which are captured in or referenced by the compliance token. An arbitration engine (330) accepts multiple governed outputs (e.g., models A/B) and resolves conflicts using: (i) deterministic precedence (primary capture beats derivative analytics), (ii) threshold-based gating (minimum confidence/interpretability encoded in token fields), and (iii) policy-governed stochastic weighting. If no candidate meets thresholds, escalation routes to supervisory review.

A glyph rendering engine converts explainability/compliance states into role-sensitive glyphs for clinicians, compliance officers, regulators, and patients. Glyph instances are cryptographically signed, linked to the underlying token, and recorded in the glyph log and immutable ledger. Machine-readable glyphs (e.g., QR/NFC/FHIR-coded events) allow downstream systems to verify and act on compliance state. In accessibility or high-noise settings, auditory and haptic glyphs provide redundant cues; failure to render required glyphs enforces fail-safe behavior.

The glyph events and explainability metrics produced in FIG. 3 are bound to compliance tokens and forwarded into the audit ledger of FIG. 4, ensuring that each AI output and symbolic rendering is cryptographically tied to the unified governance architecture of FIG. 1 and FIG. 2.

FIG. 4—Compliance Auditing and Immutable Registry

FIG. 4 is a block diagram illustrating compliance auditing of data exports. Export driver modules (410, 412) transmit normalized patient data to a compliance token generator (420). The compliance token generator (420) binds identifiers, timestamps, jurisdictional codes, and digital signatures to each export event. Tokens are then transmitted to an immutable audit ledger (430), which is implemented as a Merkle tree (432). The compliance token (422) is cross-signed by a hospital node (440) and a regulator node (442) before being committed to the ledger (430). A user interface dashboard (450) displays audit events, showing provenance metadata, signatures, and ledger state in real time.

FIG. 4 details generation and registry of compliance tokens emitted by export drivers. The token generator encapsulates identifiers, timestamps, jurisdictional overlays, policy directives, hashes, schema/version IDs, and digital signatures. Each tokened event is appended to an immutable audit ledger (e.g., Merkle-linked), producing batch-level root commitments suitable for independent verification and legal admissibility. Optional cross-signing by hospital/regulator/patient-portal nodes provides multi-party non-repudiation. Revocation events (e.g., consent withdrawal or policy change) publish revocation tokens; federated validators enforce cascading invalidation so downstream artifacts relying on a revoked token cannot execute or be exported.

The compliance tokens, revocation cascades, and arbitration outcomes maintained in FIG. 4 are derived from the secure capture, validation, high-frequency, and AI export subsystems of FIGS. 1-3, thereby demonstrating that the auditing infrastructure is not a separate invention but the integrated enforcement layer of the overall governance system.

Validators, Quarantine, and Fail-Safe Behavior

Boundary validators enforce HL7 v2/FHIR/DICOM/X12 and local schemas; they may employ ML-assisted anomaly detection to surface corrupted or adversarial inputs. Quarantined objects are isolated in a protected partition/queue/container with immutable logs of reason codes, timestamps, and linkage to any superseding corrected artifacts. Fail-safe logic denies or degrades execution whenever (a) identity cannot be assured, (b) schema/policy checks fail, (c) token signatures cannot be verified, (d) revocation propagation is incomplete, or (e) required glyph acknowledgments are missing.

Consent, Jurisdictional Overlays, and Revocation Cascade

A consent management engine generates and propagates revocation tokens that reference dependent tokens and artifacts. A jurisdictional overlay layer enforces locality-specific mandates (e.g., HIPAA retention, GDPR erasure, EU AI Act transparency). Propagation occurs in near real time subject to network conditions; validators enforce cascade on ingress/egress so governed data cannot bypass revocation. Consent state is surfaced via consent glyphs that update promptly and are bound to audit entries.

Glyphs, Libraries, and Logging

Glyph events are serialized into glyph logs containing glyph ID, timestamp, role context, event type (regulatory predicate, break-glass, consent change, audit trigger), cryptographic signature, and ledger reference. Break-glass glyphs are rendered contemporaneously with authorized overrides; regulatory predicate glyphs signal satisfaction of compliance requirements (e.g., HIPAA suppression, CMS export, FDA package generation, JCAHO/ISO/EU AI Act markers). A signed, version-controlled glyph library defines visual/auditory/haptic/machine-readable forms; updates are distributed with integrity verification, staged rollout, and rollback procedures, and each update is logged in the immutable registry.

Arbitration Engine

The arbitration engine consumes governed outputs and their associated tokens. It compares provenance, timestamps, jurisdictional tags, explainability metrics, and confidence thresholds; applies precedence rules; optionally applies policy-encoded stochastic weighting; and either selects a single enforced output or escalates to supervised adjudication. Decisions are signed in an HSM/TEE and recorded in the ledger with all inputs and policies referenced by hash to preserve privacy and auditability.

Orchestration and Policy Enforcement

A policy repository maintains active governance rules with versioning and jurisdictional scoping. The orchestration engine queries this repository to enforce binding constraints on scheduling, access, arbitration, and exports. When policy changes, dependent jobs and tokens are reevaluated; non-compliant operations are halted or rerouted and the change event is logged with Merkle commitments for third-party verification.

Interoperability and Export Drivers

Export drivers normalize governed artifacts for heterogeneous recipients (e.g., AI subsystems, EHRs, imaging archives, billing/claims). Supported exchanges include HL7 v2, FHIR resources, DICOM, and ANSI X12 (e.g., 837) where applicable. Exports embed or reference jurisdictional tags and token identifiers so downstream systems can automatically apply correct constraints and verify lineage. Batch and streaming modes share the same compliance checks; delivery acknowledgments and any rejection events are immutably logged.

Security, Auditability, and Legal Admissibility

Encryption in transit (e.g., TLS 1.3 with mutual auth/cert pinning) and at rest (e.g., AES-256 with HSM-managed keys) protects artifacts and tokens. The immutable audit ledger is append-only and cryptographically linked so entries cannot be altered without detection; batch Merkle roots enable efficient third-party audit. Optional multi-party cross-signing enhances non-repudiation. All governance events (validation, arbitration, export, revocation, glyph rendering) are logged with sufficient metadata to support regulatory reviews, incident response, and litigation.

The validators, quarantine modules, glyph rendering subsystems, revocation overlays, and fail-safe mechanisms described herein are not separate inventions but apply uniformly across the embodiments of FIGS. 1-4. Each of these shared components operates on governed data objects bound by compliance tokens and recorded in the immutable audit ledger, thereby confirming that the embodiments of FIGS. 1-4 are interdependent subsystems of a single governance architecture.

Glossary of Definitions

Compliance Token—A compliance token is a cryptographically bound data structure that encapsulates metadata associated with a validated artifact. The token binds identifiers, jurisdictional tags, policy constraints, timestamps, hashes, escalation codes, and digital signatures into a single governed record, ensuring downstream enforcement of governance rules and auditability. Token fields may encode confidence thresholds, arbitration parameters, and may embed glyph references or hashes.

Governance Metadata—Governance metadata refers to structured attributes applied automatically to each ingested data object, comprising provenance identifiers, cryptographic attributes, and jurisdictional codes. Governance metadata persist throughout the lifecycle of the object, ensuring that every subsequent process step inherits, verifies, and enforces policy lineage.

Arbitration Engine—An arbitration engine is a subsystem configured to receive multiple AI-generated or governed outputs, evaluate associated compliance tokens, and resolve conflicts under encoded policy rules. Arbitration may include deterministic logic, policy-governed stochastic weighting encoded in token fields, and threshold-based escalation, with all outcomes cryptographically signed and immutably logged.

Immutable Audit Ledger—An immutable audit ledger is an append-only, cryptographically linked record of governance events. The ledger may be implemented as a Merkle tree, distributed ledger, or tamper-evident log. Each entry is linked to its predecessor, preventing alteration and enabling forensic reconstruction and regulatory verification.

Symbolic Glyph Rendering—Symbolic glyph rendering refers to the transformation of validated data into standardized symbolic representations for use in clinical and compliance workflows. Glyphs may be visual icons, auditory cues, haptic signals, or machine-readable codes, and are designed to provide consistent interpretation of patient status, regulatory predicates, overrides, and compliance signals across human and automated systems.

Break-Glass Glyph—A break-glass glyph is a glyph rendered when an authorized user bypasses a policy constraint under emergency conditions. The break-glass glyph is generated contemporaneously with the override, cryptographically signed, and logged to the audit subsystem to ensure that the override is verifiable, non-repudiable, and regulator-auditable.

Regulatory Predicate Glyph—A regulatory predicate glyph is a glyph generated to denote satisfaction of a compliance requirement such as HIPAA suppression, CMS audit export, FDA device trial package generation, Joint Commission (JCAHO) standards, ISO/IEC codes, or EU AI Act mandates. Such glyphs provide symbolic confirmation of compliance events for regulators, auditors, and clinical users.

Consent Glyph—A consent glyph is a glyph representing the real-time consent status of a patient. Consent glyphs may display when consent is active, change state when consent is revoked, and are updated with sub-second latency. Consent glyphs are cryptographically linked to audit logs and may be displayed to patients through portals or bedside devices.

Role-Sensitive Glyph—A role-sensitive glyph is a glyph whose appearance varies depending on the role of the viewer (clinician, compliance officer, regulator, or patient). Although role-sensitive glyphs may differ in visual, auditory, or haptic form, they remain cryptographically tied to a unified audit record.

Cryptographically Signed Glyph—A cryptographically signed glyph is a glyph bound to a digital signature or cryptographic proof to ensure authenticity and integrity. Such glyphs may be embedded directly into compliance tokens, recorded in immutable audit ledgers, and verified by regulators or auditors.

Auditory Glyph—An auditory glyph is a glyph rendered as a sound, tone, or spoken alert. Each auditory glyph is cryptographically bound to compliance events and is suitable for accessibility or high-noise environments.

Haptic Glyph—A haptic glyph is a glyph rendered as tactile or vibration feedback. Haptic glyphs provide redundant safety cues in high-stress clinical settings and support accessibility requirements.

Glyph Log—A glyph log is a structured record of glyph events comprising fields such as glyph identifier, timestamp, role context, event type, cryptographic signature, and ledger reference. Glyph logs may be expressed in JSON, HL7 FHIR extensions, XML, or other machine-readable formats, enabling interoperability across clinical and regulatory systems.

Cross-Signed Glyph—A cross-signed glyph is a glyph event cryptographically signed by multiple counterparties such as a hospital node, a regulator node, and a patient portal. Cross-signing ensures glyph events cannot be repudiated by any single party and provides verifiable, multi-party compliance evidence.

Glyph Library—A glyph library is a standardized, machine-readable collection of glyphs comprising predefined visual, auditory, haptic, and machine-readable forms. Glyph libraries may be dynamically updatable, version-controlled, and cryptographically signed. Updates may be distributed under subscription or licensing models and logged in immutable audit ledgers for regulatory traceability.

Fail-Safe Mode—Fail-safe mode refers to a resilience mechanism by which the system prevents unvalidated or non-compliant transactions from executing. Fail-safe behaviors include denial of service, degraded operation with flagged outputs, or rerouting through redundant validators to preserve compliance during partial outages. In glyph embodiments, fail-safe mode may prevent downstream actions if required glyphs cannot be rendered or verified.

Policy Repository—A policy repository is a centralized, machine-readable, version-controlled store of active governance rules. The orchestration engine queries the repository in real time to enforce data access, scheduling, arbitration, and export constraints. Updates are logged, auditable, and may incorporate jurisdiction-specific directives.

User-Role Differentiation—User-role differentiation refers to a governance control framework in which clinicians, administrators, researchers, and external partners are granted only the minimum governed dataset necessary for their role. Access is dynamically enforced, logged, and revocable under policy changes or incident response events.

Federated Validator—A federated validator is a distributed compliance service deployed at subsystem boundaries such as EHRs, bedside monitors, imaging systems, or external analytics. Each validator enforces schema conformance and governance grammar before data can cross into or out of the governed system and propagates cascading invalidation on token revocation.

Quarantine Module—A quarantine module is a subsystem configured to isolate non-compliant or rejected data objects. Quarantine may be implemented as a partition, queue, or container, with each event cryptographically logged.

Specification & Validation Engine—A specification and validation engine is a component of the compliance token generator that defines schema templates (HL7, FHIR, JSON, XML) and validates tokens against those templates.

Jurisdictional Overlay—A jurisdictional overlay is a rule layer applied to revocation propagation that enforces region-specific regulatory obligations such as HIPAA retention, GDPR erasure, or EU AI Act transparency.

Merkle Root Commitment—A merkle root commitment is a top-level cryptographic hash representing the state of a Merkle tree, providing immutable evidence admissible in audits and legal proceedings.

User Interface Dashboard—A user interface dashboard is a graphical interface comprising panels for monitoring capture, validation, export, arbitration, consent, glyph rendering, and compliance audit logs.

Federated Compliance Engine—A federated compliance engine is a module that applies governance policies across distributed data flows by combining token generation, registry logging, and export driver enforcement.

Explainability Metric—An explainability metric is a confidence score, safety threshold, or interpretability indicator generated by an AI subsystem. Such metrics may be bound to compliance tokens, used for threshold enforcement, and rendered as glyphs to communicate clinical explainability.

Central Repository—A governed clinical data store for validated and normalized patient data, supporting controlled read/write access, schema conformance, and retention management. Unlike the immutable audit ledger, the central repository may allow updates and corrections under governance rules.

Immutable Audit Ledger—An append-only, cryptographically linked log of compliance events, including token issuance, arbitration outcomes, export transactions, and revocation cascades. Unlike the central repository, the audit ledger does not store patient records but instead provides non-repudiable evidence of governance actions.

The invention claimed is:

1. A system for collecting, validating, storing, and providing patient data, the system comprising:

a) one or more secure capture modules, each secure capture module comprising at least one of a digital black box, a device interface, or a manual approval interface, and each secure capture module being configured to record patient data;

b) a patient identification and data validation subsystem configured to associate the recorded patient data with an individual patient and to validate the recorded patient data to generate identified and validated data sets;

c) a central repository configured to store the identified and validated data sets;

d) a data analysis engine configured to remove personal health information from the identified and validated data sets and to execute machine-based data-affinity analysis operations on the data to detect association errors or other data-integrity issues; and e) an export driver subsystem comprising a plurality of export drivers, each export driver being configured to execute machine-formatting, normalization, filtering, and consistency-checking operations on the identified and validated data sets processed by the data analysis engine and to format the processed data for receipt by a corresponding receiving subsystem, wherein at least two of the receiving subsystems are configured to receive data in different data formats.

2. The system of claim 1, wherein the patient data recorded by the secure capture modules includes high-frequency data.

3. The system of claim 1, wherein at least one receiving subsystem comprises an artificial intelligence subsystem configured to execute machine-learning processes.

4. The system of claim 2, wherein the system is further configured to automatically route the high-frequency data to an artificial intelligence subsystem configured to execute machine-learning processes.

5. The system of claim 1, wherein the secure capture modules comprise a medical device data system configured to record patient data from medical devices.

6. The system of claim 5, wherein the medical device data system is configured to provide the recorded patient data to the patient identification and data validation subsystem.

7. The system of claim 6, wherein the recorded patient data includes environmental condition data machine-associated with the time the patient data was recorded.

8. The system of claim 1, wherein the recorded patient data includes a timestamp applied at the time of recording.

9. The system of claim 1, wherein the recorded patient data includes location information indicating where the data was recorded.

10. The system of claim 1, wherein each identified and validated data set includes patient identification data, a patient identification code, time-segment information, and patient data associated with respective time segments, and wherein the patient identification and data validation subsystem includes a human-input interface configured to receive human confirmation input in a machine-interpretable form for each identified and validated data set.

11. The system of claim 1, wherein the data analysis engine is configured to detect association errors or time-segment errors and to output machine-generated review data identified for presentation through the human-input interface.

12. The system of claim 1, wherein the system is configured to store a corrected data set after a correction is confirmed via the human-input interface and to apply a machine-executed cryptographic signature operation to the corrected data set before providing the corrected data set to a receiving subsystem.

* * * * *